United States Patent [19]

Klaue

[11] Patent Number: 4,838,252
[45] Date of Patent: Jun. 13, 1989

[54] OSTEOSYNTHETIC COMPRESSION PLATE

[75] Inventor: Kaj Klaue, Sierre, Switzerland

[73] Assignee: Synthes, Paoli, Pa.

[21] Appl. No.: 893,705

[22] Filed: Aug. 6, 1986

[30] Foreign Application Priority Data

Aug. 30, 1985 [CH] Switzerland .............. 03752/85

[51] Int. Cl.$^4$ .............................................. A61F 5/04
[52] U.S. Cl. ......................... 128/92 YP; 128/92 YL
[58] Field of Search ................. 128/92 YP, 92 YL

[56] References Cited

U.S. PATENT DOCUMENTS

| 3,463,148 | 8/1969 | Treace | 128/92 YP |
| 4,219,015 | 8/1980 | Steinemann | 128/92 YP |
| 4,503,848 | 3/1985 | Caspar et al. | 128/92 YP |

FOREIGN PATENT DOCUMENTS

| 1112803 | 11/1981 | Canada | 128/92 YP |
| 0181433 | 5/1986 | European Pat. Off. | |
| 8431616 | 2/1985 | Fed. Rep. of Germany. | |
| 3442004 | 4/1986 | Fed. Rep. of Germany. | |
| 1505513 | 11/1967 | France. | |
| 2466977 | 10/1979 | France. | |
| 335797 | 3/1959 | Switzerland | 128/92 YL |

Primary Examiner—C. Fred Rosenbaum
Assistant Examiner—Mark F. Colosimo
Attorney, Agent, or Firm—Davis Hoxie Faithfull & Hapgood

[57] ABSTRACT

An osteosynthetic compression plate with holes for the insertion of bone screws, with a cross-section that is trapezoidal or otherwise provides for a decreased plate surface against the bone while providing necessary rigidity.

6 Claims, 1 Drawing Sheet

OSTEOSYNTHETIC COMPRESSION PLATE

This invention relates to an osteosynthetic compression plate used in the treatment of bone fractures or osteotomies, and in particular to a compression plate having a reduced area of bone contact.

Osteosynthetic compression plates have been known for a long time; Swiss Pat. No. 462,375 is an example.

The predominant theory of "stress shielding" teaches that relieving the stresses on a fracture bone by means of a rigid compression plate leads to weakening of the bone. This results in failure of the bone fracture to heal, secondary fractures, or both. Attempts have therefore been made to create osteosynthetic compression plates that are less rigid, for example by putting cross grooves on them.

The rigidity of an osteosynthetic compression plate is determined by three factors: (1) the polar moment of inertia, which affects torsional rigidity, (2) the bi-axial moment of inertia, which affects bending rigidity, and (3) the cross-sectional area perpendicular to the longitudinal axis, which affects tensile rigidity. To ensure an adequate splint effect, these rigidity factors must not drop below certain thresholds, and prior attempts at avoiding the adverse affects of bone plates have not achieved the desired combination of rigidity factors for an adequate splint effect.

Accordingly, there has been a need for an osteosynthetic compression plate which would be effective for its desired purpose, i.e., as a splint, but which would not promote bone weakening or secondary fractures.

The osteosynthetic compression plate of the invention comprises an elongated plate with a plurality of holes for the insertion of bone screws arranged in the plate's longitudinal direction. The cross-section perpendicular to the longitudinal axis, rather than being essentially rectangular, in at least one segment of the plate opens out and away from the surface where the plate is applied to the bone. In a preferred embodiment of the invention, the cross-section is a trapezoid, with the shorter parallel side being the side that is applied to the bone. It has been found that such osteosynthetic compression plates permit improved blood circulation in the bone while providing the rigidity necessary for a satisfactory splint effect.

Figure 1:
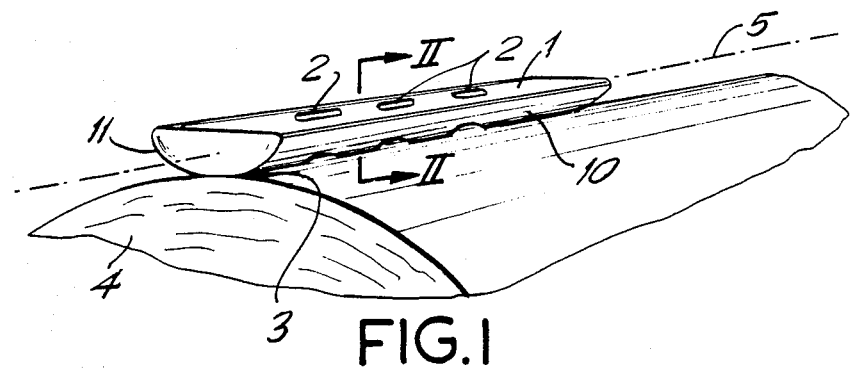
FIG. 1 shows a perspective view of one form of the osteosynthetic compression plate of the invention applied to a bone.
Figure 2:
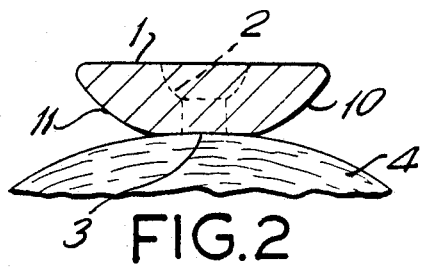
FIG. 2 shows a cross-section taken at II—II in FIG. 1 perpendicular to the longitudinal axis of the compression plate.
Figure 3:
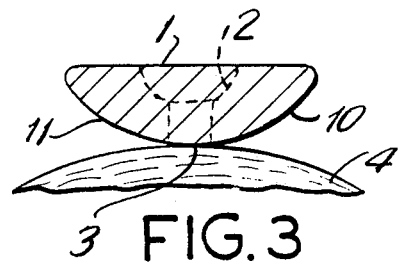
FIG. 3 shows a cross-section perpendicular to the longitudinal axis of another form of a compression plate according to the invention.

Referring to FIGS. 1 to 3, a compression plate according to the invention has an upper surface 1 and side walls 10 and 11 which taper inwardly (toward the longitudinal axis 5) to a lower surface 3 adapted to contact a bone, shown schematically as 4. A plurality of holes 2 are provided for receiving bone screws (not shown) for securing the plate to the bone. These holes are located essentially along the longitudinally axis 5 of the plate.

As shown in FIG. 2, the surface of contact of the plate with the bone is an area considerably less than the area of the upper plate surface 1. Depending on the configuration of the plate the locus of points of contact between the lower surface and the bone may be reduced to a line parallel to the axis of the plate and interrupted by the holes 2, as shown in FIG. 3 where the lower surface is a continuous curve. The plate is intended to fit snugly to the bone so that there is always less than 50 microns between the lower surface 3 of the plate and the opposing bone surface.

In the embodiment of FIGS. 1 to 3 the side walls 10 and 11 of the plate are curved convexly outwardly. The shape of the sidewalls may vary substantially and the cross-section of the plate need not be symmetrical about an axis normal to its upper surface, i.e., the shape of the right hand side of the cross-section in FIGS. 2 and 3 may differ from the left hand side.

Figure 4:
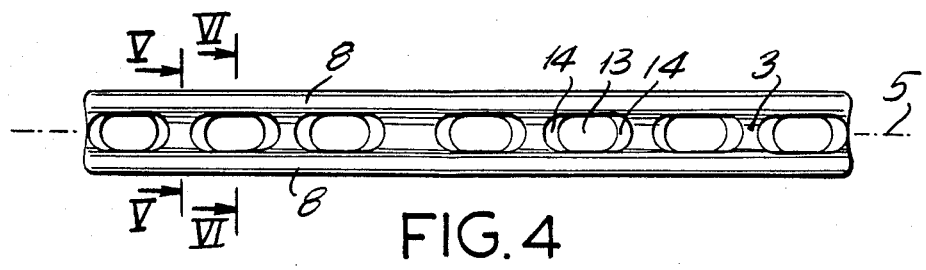
FIG. 4 shows a bottom view of still another form of compression plate according to the invention.
Figure 5:
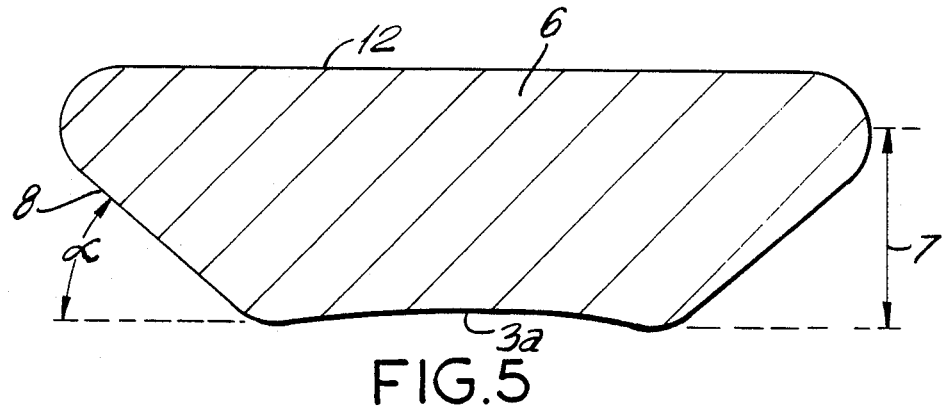
FIG. 5 shows a cross-section perpendicular to the longitudinal axis of the compression plate taken at line V—V of FIG. 4.
Figure 6:
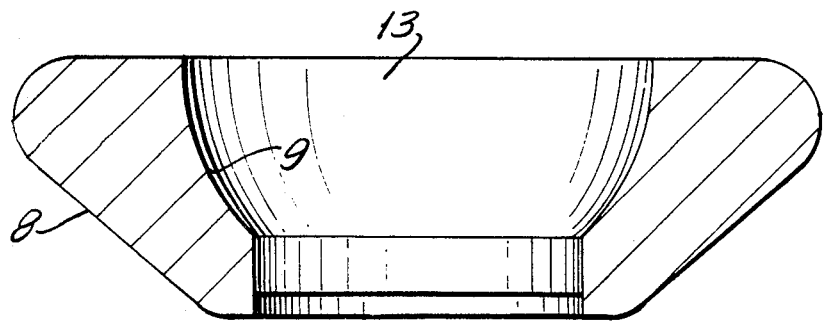
FIG. 6 shows a cross-section perpendicular to the longitudinal axis of the compression plate taken at line VI—VI of FIG. 4.

In the embodiment of FIGS. 4 to 6, the plate's upper surface 12 is connected to the lower bone application surface 3a via sidewalls 8, which form an exterior angle (alpha) of 40°, with a lateral extension of the lower surface 3a. Depending on the specific use to which the plate is to be put different angles may be used ranging from about 10° to about 70°, preferably 30° to 50°. The angles need not be the same on both sides.

As shown in FIG. 5 the surface 3a may be curved slightly to conform more closely to the bone surface.

As shown in FIGS. 4 to 6, the screw holes 13 which penetrate the plate are located along the axis 5 and have the configuration shown in U.S. Pat. No. 4,493,317, with undercut areas 14 at each end and a more or less spherical upper portion 9. Holes of other shapes may be used, for example, those shown in U.S. Pat. No. RE 28,841 or in U.S. Pat. No. 4,513,744.

In the embodiment of FIGS. 4 to 6, the cross-section 6 of the plate opens out, or increases in width, in linear fashion from surface 3a, so that in the region 7 it has the form of a truncated cone. For ease of manufacture the cross-section then narrows to the upper surface 12. Alternatively the cross-section may open out non-linearly from the bone application surface 3a, the important principle being that the bone application surface is reduced in comparison to conventional designs. The shape may for example by ellipsoid or parabolic.

Although the embodiment of the invention shown in FIGS. 4 to 6 has a lower surface 3a which is of the same width along the length of the plate, it is not necessary that this be so. Thus for example, the width of the lower surface may narrow between the screwholes.

Compression plates according to the invention retain the advantages of conventional high rigidity plates (such as the widely used 12×3.9 mm plate having an essentially rectangular cross-section) without the disadvantages which result from their extensive coverage of the bone. Surprisingly, it has been found that when the center of the mass of the rigid compression plate is moved away from the bone, the concomitant reduction of bone coverage results in improved circulation and decreased osteoporosis. These effects, in turn, lead to improved healing and the prevention of secondary fractures. A further advantage of the invention is that the decreased contact between the compression plate and the bone transfers the pressure of the screw head through the plate to the bone close to the screw axis. Therefore, only minimally disruptive torsion effects (determined by the rigidity of the compression plate) act on the bone.

In plates according to the invention, the bone application surface is not interrupted by grooves or similar recesses, so that the splint effect of the compression plate is maintained along its full length. The inclination of the sides of the plate (e.g. 40°) produces laterally wide-angled bone lamellae when the bone has healed. Because of these lamellae, there is minimal concentration of stress on the bone when the implant is removed. In addition, the angled sides make removal of the compression plate easier.

What is claimed is:

1. An osteosynthetic compression plate having:
   a top surface,
   a bone application surface,
   lateral surfaces connecting the top surface with the bone application surface wherein the lateral surfaces form an exterior angle with a lateral extension of the bone application surface in the range from about 10° to about 70°, and
   a plurality of holes extending through the plate from the top surface to the bone application surface for the insertion of bone screws, said plate having a cross-section perpendicular to the longitudinal direction, which, over substantially the entire length of the plate, is wider towards the top surface than it is at the bone application surface.

2. An osteosynthetic compression plate according to claim 1 wherein the lateral surfaces form an exterior angle with a lateral extension of the bone application surface in the range from 30° to 50°.

3. An osteosynthetic compression plate according to claim 2 wherein the lateral surfaces form an exterior angle with a lateral extension of the bone application surface of about 40°.

4. An osteosynthetic compression plate according to claim 1 wherein the cross-section is substantially trapezoidal.

5. An osteosynthetic compression plate according to claim 1 where the cross-section increases in width linearly.

6. An osteosynthetic compression plate according to claim 1 wherein said bone application surface is convexly curved, whereby the locus of the points of contact between said surface and a bone will be essentially a line broken by said holes.

* * * * *

UNITED STATES PATENT AND TRADEMARK OFFICE
CERTIFICATE OF CORRECTION

PATENT NO. : 4,838,252

DATED : June 13, 1989

INVENTOR(S) : Dr. Kaj Klaue

It is certified that error appears in the above-identified patent and that said Letters Patent is hereby corrected as shown below:

Title page, Assignee designation, delete "Synthes, Paoli, Pa." and substitute therefor --Synthes (U.S.A.), Paoli, Pa.--.

Signed and Sealed this

Twenty-seventh Day of February, 1990

Attest:

JEFFREY M. SAMUELS

*Attesting Officer*   *Acting Commissioner of Patents and Trademarks*